United States Patent
Farina et al.

(10) Patent No.: US 11,904,088 B2
(45) Date of Patent: Feb. 20, 2024

(54) METHODS FOR MEASURING DOSE CONTENT UNIFORMITY PERFORMANCE OF INHALER AND NASAL DEVICES

(71) Applicant: Proveris Scientific Corporation, Hudson, MA (US)

(72) Inventors: Dino John Farina, Sudbury, MA (US); Zachary Pitluk, New Haven, CT (US)

(73) Assignee: Proveris Scientific Corporation, Hudson, MA (US)

( * ) Notice: Subject to any disclaimer, the term of this patent is extended or adjusted under 35 U.S.C. 154(b) by 0 days.

(21) Appl. No.: 17/869,380

(22) Filed: Jul. 20, 2022

(65) Prior Publication Data
US 2023/0181846 A1 Jun. 15, 2023

Related U.S. Application Data

(63) Continuation of application No. 16/123,937, filed on Sep. 6, 2018, now Pat. No. 11,426,540, which is a (Continued)

(51) Int. Cl.
*A61M 15/00* (2006.01)
*A61M 15/08* (2006.01)
(Continued)

(52) U.S. Cl.
CPC ........ *A61M 15/0065* (2013.01); *A61M 11/00* (2013.01); *A61M 15/00* (2013.01);
(Continued)

(58) Field of Classification Search
CPC .. A61M 15/0065; A61M 11/00; A61M 15/00; A61M 15/02; A61M 15/08;
(Continued)

(56) References Cited

U.S. PATENT DOCUMENTS

| | | |
|---|---|---|
| 3,275,744 A | 9/1966 | Dietrich |
| 4,004,550 A | 1/1977 | White et al. |

(Continued)

FOREIGN PATENT DOCUMENTS

| | | |
|---|---|---|
| JP | 2004528150 A | 9/2004 |
| WO | WO-9207600 A1 | 5/1992 |

(Continued)

OTHER PUBLICATIONS

Statistics in drug research: Methodologies and recent developments Chow & Shao—Marcel Dekker—2002; p. 128-133 (Year: 2002).*

(Continued)

*Primary Examiner* — Elliot S Ruddie
(74) *Attorney, Agent, or Firm* — Wilson Sonsini Goodrich & Rosati

(57) ABSTRACT

The methods described herein provide improvements to the measurement of dose content uniformity of inhaler and nasal devices. The methods involve analyzing and measuring a spray pattern of an emitted spray from an inhaler or nasal device. The spray pattern may be used to determine the dose content uniformity of an inhaler or nasal device.

20 Claims, 3 Drawing Sheets

Related U.S. Application Data continuation of application No. PCT/US2017/021599, filed on Mar. 9, 2017.

(60) Provisional application No. 62/306,045, filed on Mar. 9, 2016.

(51) Int. Cl.
    *A61M 11/00*           (2006.01)
    *A61M 15/02*           (2006.01)

(52) U.S. Cl.
    CPC ............ *A61M 15/02* (2013.01); *A61M 15/08* (2013.01); *A61M 15/0005* (2014.02); *A61M 15/009* (2013.01); *A61M 2205/071* (2013.01); *A61M 2205/3306* (2013.01); *A61M 2205/3327* (2013.01); *A61M 2209/02* (2013.01)

(58) Field of Classification Search
    CPC ............ A61M 15/0005; A61M 15/009; A61M 2205/071; A61M 2205/3306; A61M 2205/3327; A61M 2209/02; B65D 50/061
    USPC .................................................... 128/203.15
    See application file for complete search history.

(56) References Cited

U.S. PATENT DOCUMENTS

| | | | |
|---|---|---|---|
| 4,357,670 A | 11/1982 | McFarlane | |
| 4,415,265 A | 11/1983 | Campillo et al. | |
| 4,614,300 A | 9/1986 | Falcoff et al. | |
| 4,628,465 A | 12/1986 | Ito et al. | |
| 4,965,841 A | 10/1990 | Kaneko et al. | |
| 4,984,158 A | 1/1991 | Hillsman et al. | |
| 4,992,952 A | 2/1991 | Sasaki et al. | |
| 5,075,014 A | 12/1991 | Sullivan et al. | |
| 5,284,133 A | 2/1994 | Burns et al. | |
| 5,337,926 A | 8/1994 | Drobish et al. | |
| 5,356,049 A | 10/1994 | Harris et al. | |
| RE34,910 E | 4/1995 | Funkenbusch et al. | |
| 5,435,171 A | 7/1995 | Chino et al. | |
| 5,503,144 A | 4/1996 | Bacon | |
| 5,561,527 A | 10/1996 | Krone-Schmidt et al. | |
| 5,579,659 A | 12/1996 | Roberts et al. | |
| 5,676,129 A * | 10/1997 | Rocci, Jr. .......... | A61M 15/0083 128/200.14 |
| 5,785,048 A | 7/1998 | Koerner et al. | |
| 5,879,713 A | 3/1999 | Roth et al. | |
| 6,029,600 A | 2/2000 | Davis et al. | |
| 6,148,815 A | 11/2000 | Wolf et al. | |
| 6,149,071 A | 11/2000 | MacCallummhor et al. | |
| 6,193,936 B1 | 2/2001 | Gardner et al. | |
| 6,202,642 B1 | 3/2001 | McKinnon et al. | |
| 6,207,445 B1 | 3/2001 | Crosby | |
| 6,256,597 B1 | 7/2001 | Wang et al. | |
| 6,481,301 B2 | 11/2002 | Pawliszyn | |
| 6,508,112 B1 | 1/2003 | Verhoeven et al. | |
| 6,618,127 B2 | 9/2003 | Yang et al. | |
| 6,651,651 B1 | 11/2003 | Bonney et al. | |
| 6,665,421 B1 | 12/2003 | Farina et al. | |
| 6,785,400 B1 | 8/2004 | Farina et al. | |
| 6,799,090 B2 | 9/2004 | Farina et al. | |
| 6,973,199 B2 | 12/2005 | Farina et al. | |
| 7,100,839 B2 | 9/2006 | Farina et al. | |
| 7,463,751 B2 | 12/2008 | Farina et al. | |
| 7,490,782 B2 | 2/2009 | Farina et al. | |
| 7,658,122 B2 | 2/2010 | Farina et al. | |
| 7,672,478 B2 | 3/2010 | Farina et al. | |
| 7,686,016 B2 | 3/2010 | Wharton et al. | |
| 7,934,434 B2 | 5/2011 | Shelton et al. | |
| 8,807,131 B1 | 8/2014 | Tunnell et al. | |
| 9,360,400 B2 | 6/2016 | Farina et al. | |
| 10,473,564 B2 | 11/2019 | Farina et al. | |
| 11,426,540 B2 | 8/2022 | Farina et al. | |
| 2001/0032521 A1 | 10/2001 | Pawliszyn | |
| 2004/0199296 A1 | 10/2004 | Farina et al. | |
| 2004/0258278 A1 | 12/2004 | Farina et al. | |
| 2005/0001054 A1 | 1/2005 | Farina et al. | |
| 2005/0016527 A1 | 1/2005 | Barger et al. | |
| 2005/0068528 A1 | 3/2005 | Altobelli et al. | |
| 2005/0077369 A1 | 4/2005 | Farina et al. | |
| 2005/0147565 A1 | 7/2005 | Sequeira et al. | |
| 2006/0034504 A1 | 2/2006 | Farina et al. | |
| 2006/0102808 A1 | 5/2006 | Farina et al. | |
| 2006/0140873 A1 | 6/2006 | Chang | |
| 2007/0119450 A1 | 5/2007 | Wharton et al. | |
| 2008/0173067 A1 * | 7/2008 | Farina ..................... | B05B 11/10 73/1.16 |
| 2012/0036943 A1 | 2/2012 | Lehmann | |
| 2014/0008384 A1 * | 1/2014 | Helmlinger ......... | A61M 15/008 222/23 |
| 2015/0020804 A1 | 1/2015 | Van Der Mark et al. | |
| 2015/0157566 A1 | 6/2015 | Kim et al. | |
| 2015/0335834 A1 | 11/2015 | Anandhakrishnan | |
| 2019/0070372 A1 | 3/2019 | Farina et al. | |
| 2019/0113418 A1 | 4/2019 | Eicher et al. | |

FOREIGN PATENT DOCUMENTS

| | | |
|---|---|---|
| WO | WO-03000429 A2 | 1/2003 |
| WO | WO-02100468 A3 | 5/2003 |
| WO | WO-2004011069 A1 | 2/2004 |
| WO | WO-2017/156287 | 9/2017 |

OTHER PUBLICATIONS

Apter, et al., Testing the reliability of old and new features of a new electronic monitor for metered dose inhalers; Annals of Allergy, Asthma, & Immunology, Apr. 2001, 421-424.

Asthma Facts, Center for Disease Control, Jul. 2013, pp. 1-15.

Asthma's Impact on the Nation, Center for Disease Control, pp. 1-4.

Balderin, Amira M. Real-time analysis of fuel spray images, IEEE International Conference on Acoustics, Speech, and Signal Processing, Apr. 6-9, 1987, DOI: 10.1109/ICASSP.1987.1169740 pp. 624-624.

Bennett, J. S., An investigation of particle size measurement using non-intrusive optical techniques in a gas turbine combustor, M.S. Thesis Naval Postgraduate School, Monterey, CA, 1 pg. (abstract) (Sep. 1985).

Chow et al., Statistics in drug research: methodologies and recent developments, Marcel Decker, 2002 pp. 128-133.

Cooper, A QbD Method Development Approach for a Generic pMDI, Pharmaceutical Technology, 40.5, 30-36, 63.

Copley Scientific. Quality Solutions for Inhaler Testing. 2007; pp. 12-18 & 20; Retrieved Aug. 31, 2015, Available at: URL:https://www.copleyscientific.com.

Cost of COPD, Propeller Health, 2014, pp. 2-10.

Dhand, R. et al., High Speed Photographic Analysis of Aerosols Produced by Metered Dose Inhalers, J. Pharm Pharmacol., vol. 40,5 pgs. (abstract only) (1988).

Doub, Metered Dose Inhalers (MDIs) In Vitro Measures to Confirm Patient Perceptions: HFA vs. CFC, FDA: Bringing value to the Patent in a Changing World, Mar. 29, 2011, 1-16.

Dunbar, C.A., et al., An Experimental Investigation of the Spray Issued from a pMDI Using Laser Diagnostic Techniques, Journal of Aerosol Medicine, 10(4 ),1 pg. (abstract) , (1997).

EP15814981.5 Extended Search Report dated Apr. 17, 2018.

Everard et al. Factors Affecting Total and "Respirable" Dose Delivered by a Salbutamol Metered Dose Inhaler, Thorax 50 (1995): 746-749-455.

Ex Parte Quayle Action dated Dec. 10, 2015 for U.S. Appl. No. 14/788,324.

Extended European Search report dated Oct. 14, 2019 for EP Appl. No. 17764110.7.

Farina, et al. A Shaking Control Space Study for a Fluticasone/Salmeterol Metered Dose Inhaler Based on Spray Pattern Analysis. Proveris Scientific Corporation, 2013.

(56) References Cited

OTHER PUBLICATIONS

Feikema, D. A., Optical measurements in rocket engine liquid sprays, In Alabama Univ., Research Reports: 1994 NASA/ASEE Summer Faculty Fellowship Program 6p (See N95-18967 05-80), 1 pg. (abstract) (Oct. 1994).
Ferreira et al. Box-Behnken Design an Alternative for the Optimization of Analytical Methods. Analytica Chimica Acta 597 (2007): 179-186.
Fink et al. Problems with Inhaler Use: A Call for Improved Clinician and Patient Education, Respiratory Care, 50.10 (Sep. 2005): 1360-1375.
Giraud et al. Misuse of corticosteroid metered-dose inhaler is associated with decreased asthma stability, European Respiratory Journal, (2002): 246-251.
Guidance for Industry. Nasal Spray and Inhalation Solution, Suspension, and Spray Drug Products—Chemistry, Manufacturing, and Controls Documentation. US Department of Health and Human Services. CDER. Jul. 2002. 49 pages.
Hess, Dean R. Ph.D., RRT, FAARC, Aerosol Delivery Devices in the Treatment of Asthma, Respiratory Care, Jun. 2008, vol. 53, No. 6, pp. 699-725.
Ibrahim, et al. Inhalation drug delivery devices: Technology Update, Med Devices Auckland 8 (2015): 131-139.
International Search report dated Oct. 6, 2015 for International Application No. PCT/US2015/038658.
Kelly, Shake Well Before Dispensing, PharmaD, Pharmacy Times, Sep. 28, 2015, 1-3.
Locke, R. J., et al., Nonintrusive Laser-Induced Imaging for Speciation and Patternation in High-Pressure Gas Turbine Combustors, Proc. SPIE. vol. 3783, 12 pgs. (1999).
Lopera et al, Improved entropic edge-detection. Proceedings—International Conference on Image Analysis and Processing, ICIAP 1999. 180-184. 10.1109/ICIAP.1999.797591.
McEvoy, Mike, Alburterol (Ventolin): Drug Whys, EMSL.com.
Minnich, M. G., et al., Spatial Aerosol Characteristics of a Direct Injection High Efficiency Nebulizer via Optical Patternation, Spectrochmica Acta Part B, vol. 56, 2 pgs (abstract) , (2001).
Myrdal et al. Advances in Metered Dose Inhaler Technology: Formulation Development. AAPS Pharma Sci Tech., 15.2 (Apr. 2014): 434-44.
Al-Jahdali, et al., Improper inhaler technique is associated with poor asthma control and more frequent emergency department visits, Asthma & Clinical Immunology 2013, 9:8.
Newcomb, et al. How critical quality attributes and process variables drive the in-vitro performance of pMDIs: new technologies and methods; Proveris Scientific Corporation, 2015.
Newcomb et al., Understanding the importance and effects of shaking on pMDI performance, Proveris Scientific Corporation, DDL Poster, 2015.
Newman, Principles of Metered-Dose Inhaler Design; Respiratory Care, September, 50.9 (2005): 1177-1190.
Nicolini., Beclomethasone/Formoterol fixed combination for the management of asthma: patient considerations. Ther Clin Risk Manag, 4.5 (2008): 855-864.
Notice of Allowance dated Feb. 10, 2016 for U.S. Appl. No. 14/788,324.
Notice of Allowance dated Sep. 11, 2019 for U.S. Appl. No. 15/388,797.
Pastor, J. V., et al., Analysis Methodology of Diesel Spray and Flame by Means of In-Cylinder Endoscopic Imaging, (The Institution of Electrical Engineers). Savoy Place, London: IEE, 1 pg. (abstract), (2000).
PCT/US17/21599 International Search Report with Written Opinion, dated Jun. 1, 2017.
Pitluk et al., A Shaking Control Space for Fluticasone Propionate Nasal Spray DCU Testing. Proveris Scientific Corporation, 2012.
Sassi, G., et al., Vision system for combustion and diagnosis in gas turbines, Proc. SPIE vol. 2506, Air Pollution and Visibility Measurements, Fabian, P., et al., Eds., 1 pg. (abstract) (Sep. 1995).
Saxena, Study: Patients don't know how to use drug delivery devices; www.fiercedrugdelivery.com, Dec. 17, 2014, 1-2.
Scichilone, et al. Patient perspectives in the management of asthma: improving patient outcomes through critical selection of treatment options, Patent Preference and Adherence, 4 (2010): 17-23.
Settles, G.S., A Flow Visualization Study of Airless Spray Painting, Proceedings of the 10th Annual conference on Liquid Atomization and Spray Systems, ILASS-Americas '07, May 18-21, 1997, Ottawa, Canada, pp. 145-149.
Terzano, Pressurized metered Dose Inhalers and Add-on Devices, Pulmonary Pharmacology & Therapeutics, 14 (2001): 351-366.
The Fifth Conference of ILASS-ASIA Figs. 1-11, 4 pp.
Ullom, M. J and Sojka, P. E., A Simple Optical Patternator for Evaluating Spray Symmetry, Review of Scientific Instruments, 72(5), 1 pg. (abstract), (2001).
Virchow et al. A review of the value of innovation in inhalers for COPD and asthma, Journal of Market Access & Health Policy, Sep. 2015.
Weinstein, C. L. J., et al., Development of an Automated Digital Spray Pattern Measurement System, Respiratory Drug Delivery, VIII:581-583 (2002).

\* cited by examiner

METHODS FOR MEASURING DOSE CONTENT UNIFORMITY PERFORMANCE OF INHALER AND NASAL DEVICES

CROSS REFERENCE

This application is a continuation application of U.S. patent application Ser. No. 16/123,937, filed on Sep. 6, 2018, now U.S. Pat. No. 11,426,540, issued on Aug. 30, 2022, which is a continuation application of International Patent Application No. PCT/US2017/021599, filed on Mar. 9, 2017, which claims priority to U.S. Provisional Application No. 62/306,045, filed on Mar. 9, 2016, each of which is incorporated herein by reference in its entirety.

BACKGROUND OF THE INVENTION

The drive for an approved generic albuterol-based pMDI has significantly increased in recent years due to the cost barrier, patent expiration of reference products, and recently released draft FDA guidance documents. Product usage instructions for all of the current FDA approved albuterol pMDIs only include non-descript language for shaking the pMDI such as " . . . shake well before each use . . . " with no indication for the patient regarding shaking duration, frequency, orientation, shake-to-fire interval, or what the effects might be if the patient doesn't shake the product before use. From a formulation perspective, shaking is critical for suspension pMDIs because the active drug particles in the formulation tend to rapidly sink or rise to the liquid surface due to differences in density from the propellants.

The in-vitro spray test methods required to show bioequivalence of pMDI products from a regulatory perspective, particularly dose content uniformity (DCU) and aerodynamic particle size distribution (APSD) through-life testing, may in some instances be time intensive, complicated, and error-prone.

SUMMARY OF THE INVENTION

In one aspect, a method is provided for measuring performance of an inhaler or nasal device comprising a drug formulation, the method comprising: a) shaking the inhaler or nasal device, wherein the shaking comprises one or more shake parameters; b) actuating the inhaler or nasal device, thereby emitting a spray of the drug formulation; and c) measuring a spray pattern of the spray of the drug formulation, wherein the spray of the drug formulation comprises an emitted dose of a drug, and wherein dose content uniformity (DCU) performance of the inhaler or nasal device is determined based on the spray pattern. In some cases, the inhaler or nasal device is selected from the group consisting of: a pressurized metered dose inhaler (pMDI), a metered dose inhaler (MDI), and a nasal spray. In any of the preceding methods, the one or more shake parameters may comprise one or more of shake frequency, shake angle, shake duration, shake-to-fire interval and shake orientation. In some cases, the shake frequency comprises about 1.0 Hz to about 4.0 Hz. In any of the preceding methods, the shake angle may comprise about 30 degrees to about 180 degrees. In any of the preceding methods, the shake duration may comprise about 2 seconds to about 15 seconds. In any of the preceding methods, the shake-to-fire interval may comprise about 0 seconds to about 10 seconds. In any of the preceding methods, the shake orientation may comprise about 0 degrees to about 359 degrees. In any of the preceding methods, the drug formulation may comprise a suspension formulation. In any of the preceding methods, the drug formulation comprises one or more excipients. In any of the preceding methods, the drug formulation may comprise no excipients. In any of the preceding methods, the method may further comprise, prior to b), monitoring the one or more shake parameters. In any of the preceding methods, b) may comprise actuating the inhaler or nasal device when the one or more shake parameters have reached or have exceeded a predetermined threshold. In some cases, the predetermined threshold is determined by a composition of the drug formulation. In any of the preceding methods, the method may be performed on the inhaler or nasal device during beginning-of-life administration, middle-of-life administration, end-of-life administration or any combination thereof. In any of the preceding methods, the spray pattern may be an optical spray pattern. In any of the preceding methods, c) may further comprise illuminating the spray with an illumination device and imaging the optical spray pattern with an imaging device. In any of the preceding methods, the spray pattern may be an impaction-based spray pattern. In any of the preceding methods, the spray pattern may be presented on a report. In some cases, the spray pattern may be represented on the report as a sensitivity plot. In some cases, the sensitivity plot may be plotted as a spray pattern area as a function of the one or more shake parameters. In any of the preceding methods, the actuating may comprise a length of time a valve of the inhaler or nasal device is left open by the actuating. In any of the preceding methods, the actuating may comprise compressing the inhaler or nasal device. In some cases, the compressing may comprise a stroke length. In some cases, the stroke length may comprise about 1 millimeter to about 200 millimeters.

In another aspect, a method is provided for testing for delivery of a drug formulation with an inhaler or nasal device, the method comprising: a) monitoring two or more shake parameters; and b) actuating the inhaler or nasal device when a predetermined threshold of the two or more shake parameters is reached or exceeded, thereby emitting a spray of the drug formulation, wherein the spray of the drug formulation comprises an emitted dose of a drug. In some cases, the emitted dose of a drug may be within about 15% of a target dose content uniformity (DCU) performance. In some cases, the target DCU performance may be defined by regulatory or industry guidelines. In any of the preceding methods, the method may further comprise repeating the monitoring and actuating one or more times, thereby emitting one or more additional sprays of the drug formulation, wherein each of the one or more additional sprays may comprise an emitted dose of the drug. In some cases, each of the one or more additional sprays may comprise an emitted dose of the drug within about 15% of the target DCU performance. In any of the preceding methods, the two or more shake parameters may be selected from the group consisting of: shake duration, shake frequency, shake angle, shake-to-fire interval, and shake orientation. In any of the preceding methods, the method may further comprise, prior to a), shaking the inhaler or nasal device. In some cases, the shake duration may comprise about 2 seconds to about 15 seconds. In some cases, the shake angle may comprise about 30 degrees to about 180 degrees. In some cases, the shake frequency may comprise about 1.0 Hz to about 4.0 Hz. In some cases, the shake-to-fire interval may comprise about 0 seconds to about 10 seconds. In some cases, the shake orientation may comprise about 0 degrees to about 359 degrees. In any of the preceding cases, the monitoring may comprise measuring the two or more shake parameters. In any of the preceding cases, the drug formulation may comprise one or more excipients. In any of the preceding cases, the drug formulation may comprise no excipients. In some cases, the predetermined threshold may be determined based on (i) a number of the one or more excipients present in the drug formulation, (ii) a composition of the one or more excipients present in the drug formulation, or (iii) a combination of both. In some cases, each of the one or more additional sprays may comprise an emitted dose of the drug within about 15% of the target DCU performance at each of beginning-of-life administration, middle-of-life administration and end-of-life administration. In any of the preceding methods, the method may further comprise administering the emitted dose of a drug to a patient in need thereof. In any of the preceding methods, the method may further comprise, after the actuating, performing a spray pattern analysis on the spray. In some cases, the method may further comprise, determining an amount of the emitted dose of a drug from the spray pattern analysis. In some cases, performing the spray pattern analysis may comprise measuring an optical spray pattern of the spray. In some cases, measuring the optical spray pattern of the spray may comprise illuminating the spray with an illumination device and imaging the optical spray pattern with an imaging device. In some cases, performing the spray pattern analysis may comprise measuring an impaction-based spray pattern of the spray. In any of the preceding methods, the inhaler or nasal device may be selected from the group consisting of: a pressurized metered dose inhaler (pMDI), a metered dose inhaler (MDI), and a nasal spray. In any of the preceding claims, the drug formulation may comprise a suspension formulation. In some cases, the spray pattern analysis may be presented on a report. In some cases, the spray pattern analysis may be represented on the report as a sensitivity plot. In some cases, the sensitivity plot may be plotted as a spray pattern area as a function of at least one of the two or more shake parameters. In any of the preceding methods, the actuating may comprise a length of time a valve of the inhaler or nasal device is left open by the actuating. In any of the preceding methods, the actuating may comprise compressing the inhaler or nasal device. In some cases, the compressing may comprise a stroke length. In some cases, the stroke length may comprise about 1 millimeter to about 200 millimeters.

In another aspect, a method is provided for testing for delivery of a drug formulation with an inhaler or nasal device, the method comprising: a) monitoring one or more shake parameters, wherein at least one of the one or more shake parameters comprises shake angle, shake frequency, shake-to-fire interval, or shake orientation; and b) actuating the inhaler or nasal device when a predetermined threshold of the one or more shake parameters is reached or exceeded, thereby emitting a spray of the drug formulation, wherein the spray of the drug formulation comprises an emitted dose of a drug. In some cases, the emitted dose of a drug may be within about 15% of a target dose content uniformity (DCU) performance. In some cases, the DCU performance may be defined by regulatory or industry guidelines. In any of the preceding methods, the method may further comprise repeating the monitoring and actuating one or more times, thereby emitting one or more additional sprays of the drug formulation, wherein each of the one or more additional sprays comprises an emitted dose of the drug. In some cases, each of the one or more additional sprays may comprise an emitted dose of the drug within about 15% of the target DCU performance. In any of the preceding methods, the one or more shake parameters may further comprise shake duration. In any of the preceding methods, the method may further comprise, prior to the monitoring, shaking the inhaler or nasal device. In some cases, the shake duration may comprise about 2 seconds to about 15 seconds. In any of the preceding methods, the shake angle may comprise about 30 degrees to about 180 degrees. In any of the preceding methods, the shake frequency may comprise about 1.0 Hz to about 4.0 Hz. In any of the preceding methods, the shake-to-fire interval may comprise about 0 seconds to about 10 seconds. In any of the preceding methods, the shake orientation may comprise about 0 degrees to about 359 degrees. In any of the preceding methods, the monitoring may comprise measuring the one or more shake parameters. In any of the preceding methods, the drug formulation may comprise one or more excipients. In any of the preceding methods, the drug formulation may comprise no excipients. In some cases, the predetermined threshold may be determined based on (i) a number of the one or more excipients present in the drug formulation, (ii) a composition of the one or more excipients present in the drug formulation, or (iii) a combination of both. In some cases, each of the one or more additional sprays may comprise an emitted dose of the drug within about 15% of the target DCU performance at each of beginning-of-life administration, middle-of-life administration and end-of-life administration. In any of the preceding methods, the method may further comprise administering the emitted dose of a drug to a patient in need thereof. In any of the preceding methods, the method may further comprise, after the actuating, performing a spray pattern analysis on the spray. In any of the preceding methods, the method may further comprise, determining an amount of the emitted dose of a drug from the spray pattern analysis. In some cases, performing the spray pattern analysis may comprise measuring an optical spray pattern of the spray. In some cases, measuring the optical spray pattern of the spray comprises illuminating the spray with an illumination device and imaging the optical spray pattern with an imaging device. In some cases, performing the spray pattern analysis may comprise measuring an impaction-based spray pattern of the spray. In any of the preceding methods, the inhaler or nasal device may be selected from the group consisting of: a pressurized metered dose inhaler (pMDI), a metered dose inhaler (MDI), and a nasal spray. In any of the preceding methods, the drug formulation may comprise a suspension formulation. In any of the preceding methods, the spray pattern analysis may be presented on a report. In some cases, the spray pattern analysis may be represented on the report as a sensitivity plot. In some cases, the sensitivity plot may be plotted as a spray pattern area as a function of the one or more shake parameters. In any of the preceding methods, the actuating may comprise a length of time a valve of the inhaler or nasal device is left open by the actuating. In any of the preceding methods, the actuating may comprise compressing the inhaler or nasal device. In some cases, the compressing may comprise a stroke length. In some cases, the stroke length may comprise about 1 millimeter to about 200 millimeters.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 depicts consolidated optical spray pattern sensitivity profiles for three tested pMDI products as a function of shaking. The tested pMDI products are identified by the number of excipients. Auto-scaled y-axes were used to accommodate the different spray pattern area ranges for the products.

DETAILED DESCRIPTION OF THE INVENTION

Figure 1:
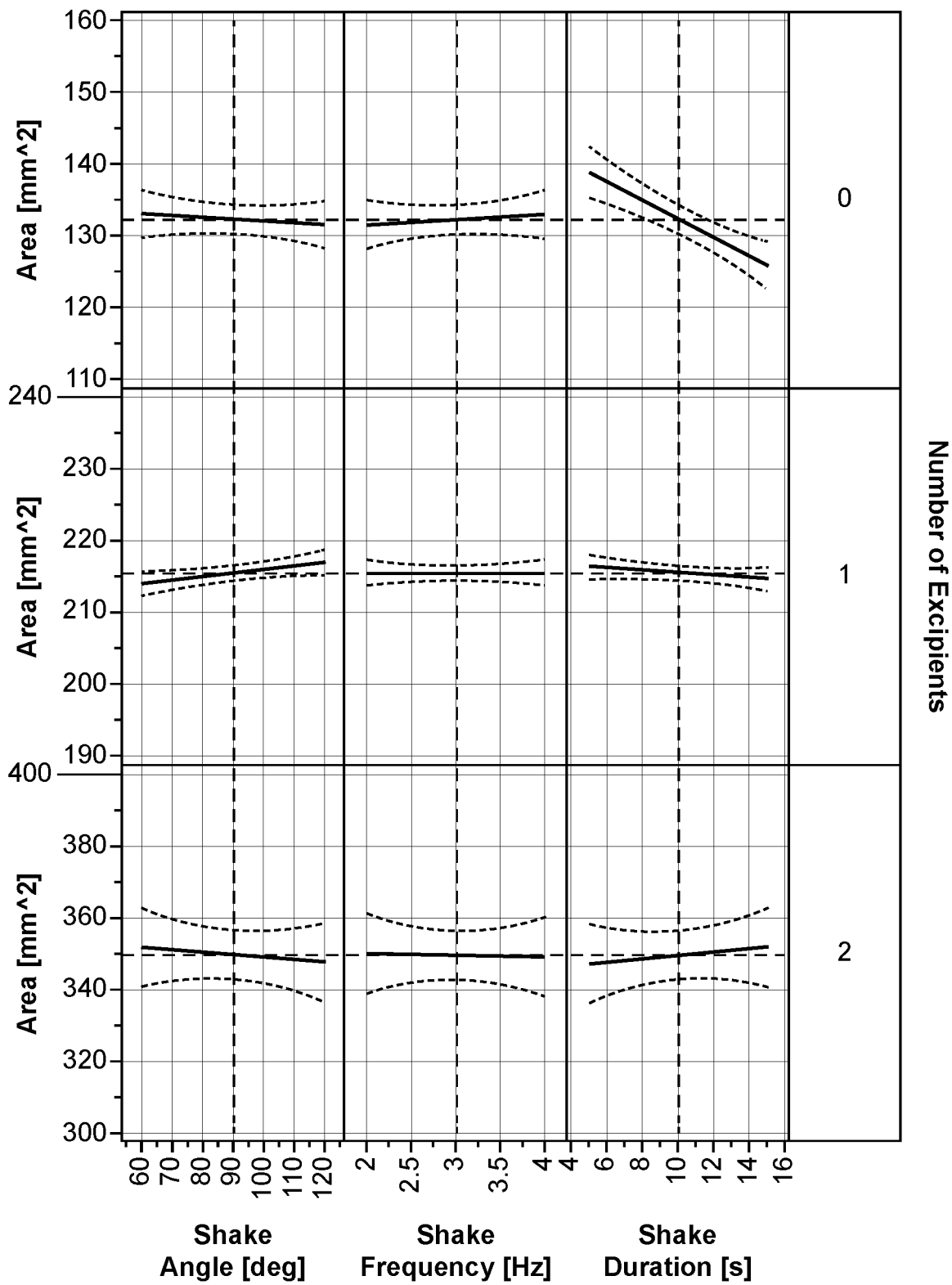
Figure 2:
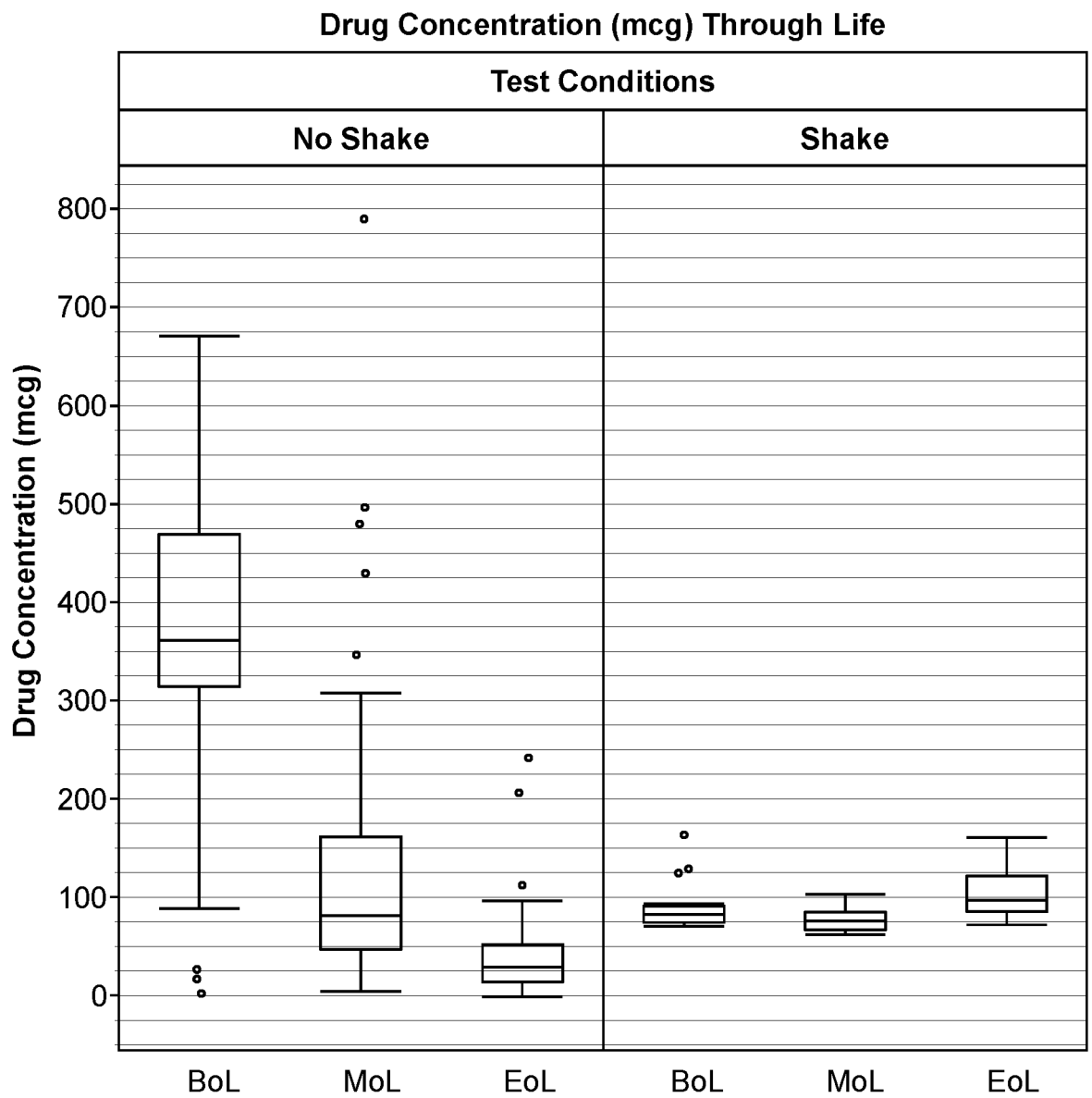
FIG. 2 depicts the effects of shaking versus not shaking on through-life DCU performance for a tested product with no excipients.
Figure 3:
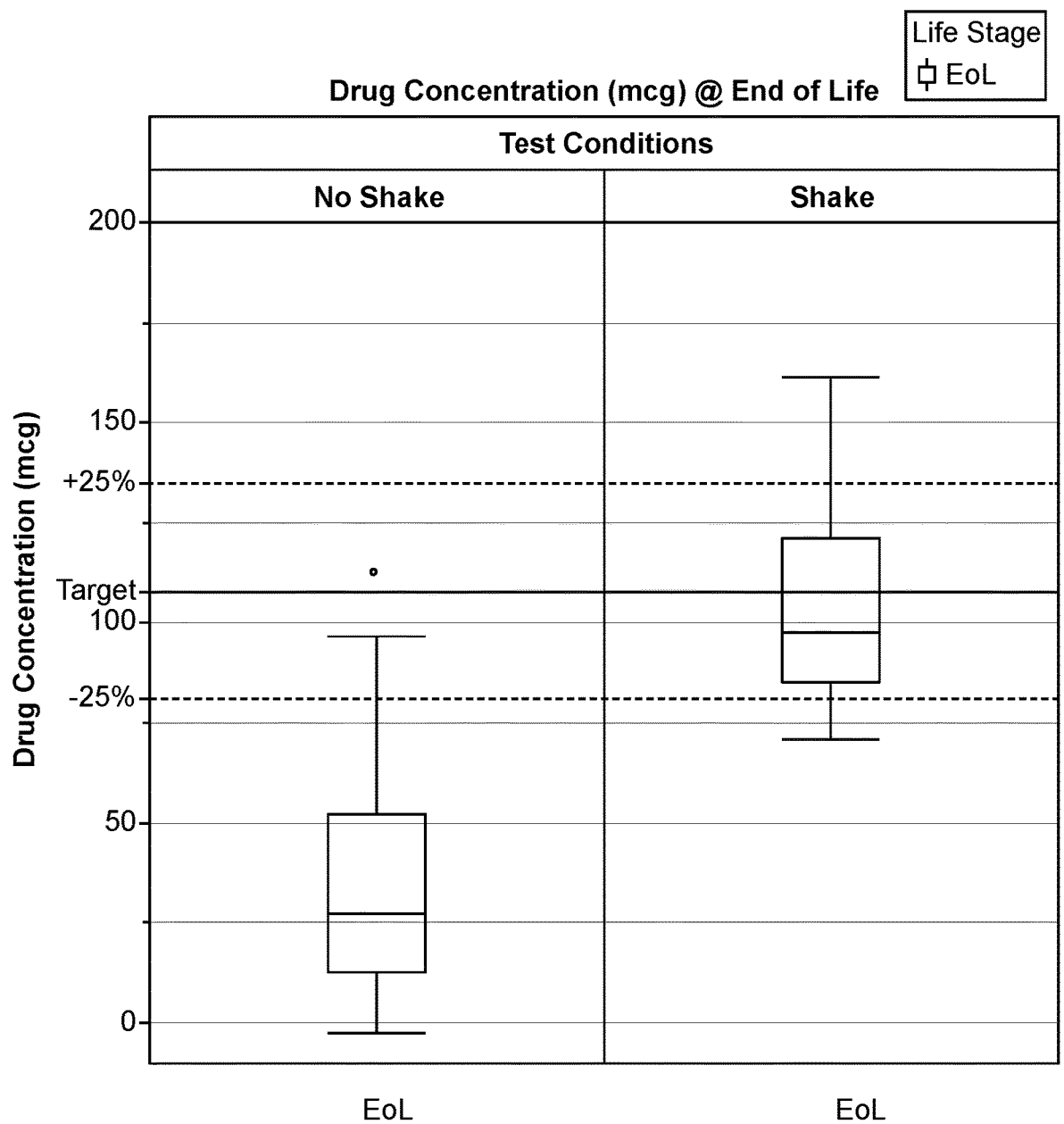
FIG. 3 depicts a detailed view of end of life DCU performance for a tested product with no excipients, with and without shaking.

The methods described herein generally relate to improving delivery of a formulation with oral inhaler or nasal devices. The methods also relate to the measurement of dose content uniformity (DCU) performance of oral inhaler or nasal devices. Oral inhaler or nasal products generally require "proper shaking" prior to actuation of the device to en sure that a target dose of drug is delivered. However, it is often unclear as to what parameters constitute "proper shaking." The dose of drug delivered by the inhaler or nasal device can be adversely affected by improper shaking, for example, not shaking long enough or not shaking at the proper angle. Further, the drug formulation may affect the shaking parameters required to achieve "proper shaking". For example, factors including the number of excipients present in the formulation, the composition of the excipients present in the formulation, as well as other physical factors may determine the shaking parameters required to achieve "proper shaking."

In some instances, the devices (e.g. oral inhalers or nasal devices) referred to herein may be sprayed (e.g. via actuation, etc) after undergoing different parameters of shaking, and a spray pattern may be measured and/or recorded for the differing parameters of shaking. Optionally, the spray patterns may be analyzed and correlated with the DCU of the formulations being administered (e.g. sprayed), and desired shake parameters may be determined, e.g. based on the correlation. Accordingly, the present methods may provide an avenue for determining desired shake parameters, tailored to specific formulations, for delivery of the formulation via the devices.

In one aspect, the methods involve measuring the performance of an inhaler or nasal device comprising a drug formulation. The method may comprise: a) shaking the inhaler or nasal device; b) actuating the inhaler or nasal device, thereby emitting a spray of the drug formulation; and c) measuring a spray pattern of the spray of the drug formulation, wherein the spray of the drug formulation comprises an emitted dose of a drug. The dose content uniformity (DCU) performance of the inhaler or nasal device may be determined based on the spray pattern.

In another aspect, the methods may involve improving delivery of a drug formulation with an inhaler or nasal device. The method may comprise: a) monitoring two or more shake parameters; and b) actuating the inhaler or nasal device when a predetermined threshold of the two or more shake parameters is reached or exceeded, thereby emitting a spray of the drug formulation, wherein the spray of the drug formulation comprises an emitted dose of a drug.

In yet another aspect, the methods may involve improving delivery of a drug formulation with an inhaler or nasal device. The method may comprise: a) monitoring one or more shake parameters, wherein at least one of the one or more shake parameters comprises shake angle, shake frequency, shake-to-fire interval, or shake orientation; and b) actuating the inhaler or nasal device when a predetermined threshold of the one or more shake parameters is reached or exceeded, thereby emitting a spray of the drug formulation, wherein the spray of the drug formulation comprises an emitted dose of a drug.

The methods disclosed herein may generally be used to measure the performance of inhaler or nasal devices. An inhaler device may be utilized for e.g., delivery of a drug or substance directly to the lungs of a subject. The methods described herein may be suitable for use with any inhaler device that requires shaking and/or actuation. In some cases, the inhaler device is a metered-dose inhaler (MDI), for example, a pressurized metered-dose inhaler (pMDI). Non-limiting examples of MDIs may include AeroChamber® and Autohaler®. In some cases, the MDI comprises a spacer or aerosol holding chamber. The inhaler device may be a dry powder inhaler, non-limiting examples including: Aerolizer®, Diskus®, Ellipta™, Flexhaler®, Handihaler®, Neohaler®, Pressair™, Twisthaler®, Rotahaler® and Turbuhaler®. In some cases, the methods may be used with a nasal device for, e.g., local delivery of a drug to the nose or the paranasal sinuses. Non-limiting examples of nasal devices may include: mechanical spray pumps (e.g., squeeze bottles, multi-dose metered-dose spray pumps, single/duo-dose spray pumps, bi-directional multi-dose spray pumps), gas-driven spray systems/atomizers, mechanical powder sprayers, breath actuated inhalers, and insufflators.

The inhaler or nasal device may be an Orally Inhaled or Nasal Drug Product (OINDP). Non-limiting examples of OINDPs which may be suitable for use with the methods described herein may include: aclidinium bromide inhalation powder (Tudorza® Pressair®), ipratropium inhalation aerosol (Atrovent® HFA), tiotropium inhalation powder Spiriva® Handihaler®), tiotropium inhalation solution (Spiriva® Respimat®), umeclidinium inhalation powder (Incruse® Ellipta®), albuterol/ipratropium inhalation solution (DuoNeb®), albuterol/ipratropium bromide inhalation spray (Combivent® Respimat®), budesonide/formoterol fumarate dihydrate inhalation aerosol (Symbicort®), fluticasone/salmeterol inhalation powder (Advair® Diskus®), fluticasone/salmeterol inhalation aerosol (Advair® HFA), fluticasone furoate/vilanterol inhalation powder (Breo® Ellipta®), mometasone furoate/formoterol fumarate inhalation aerosol (Dulera®), tiotropium bromide/olodaterol inhalation spray (Stiolto™ Respimat®), umeclidinium/vilanterol inhalation powder (Anoro® Ellipta®), beclomethasone dipropionate HFA inhalation aerosol (Qvar®), budesonide inhalation powder (Pulmicort® Flexhaler®), budesonide inhalation suspension (Pulmicort® Respules®), ciclesonide inhalation aerosol (Alvesco®), flunisolide inhalation aerosol (Aerospan®), fluticasone furoate inhalation powder (Arnuity™ Ellipta®), fluticasone propionate inhalation aerosol (Flovent® HFA), fluticasone propionate inhalation powder (Flovent® Diskus®), mometasone furoate inhalation powder (Asmanex® Twisthaler®), mometasone furoate inhalation aerosol (Asmanex® HFA), arformoterol tartrate inhalation solution (Brovana®), formoterol fumarate inhalation powder (Foradil®), formoterol fumarate inhalation solution (Perforomist®), indacaterol inhalation powder (Arcapta™ Neohaler™), olodaterol inhalation spray (Striverdi® Respimat®), salmeterol xinafoate inhalation powder (Serevent® Diskus®), albuterol sulfate inhalation powder (Proair® Respiclick®), albuterol sulfate inhalation aerosol (Proair® HFA), albuterol inhalation solution (AccuNeb®), albuterol sulfate inhalation aerosol (Proventil® HFA), albuterol sulfate inhalation aerosol (Ventolin® HFA), levalbuterol tartrate inhalation aerosol (Xopenex® HFA).

The inhaler or nasal device may include a formulation of, for example, a drug or an active ingredient. In some cases, the formulation includes one or more excipients. In some cases, the formulation does not include any excipients. In some cases, the formulation includes one or more propellants. The formulation may be a suspension, a solution, or a dry powder.

The methods may generally involve shaking the inhaler or nasal device. In some cases, shaking the inhaler or nasal device involves performing a shaking regimen with the inhaler or nasal device. A shaking regimen may include one or more shake parameters, including one or more of shake duration, shake angle, shake frequency, shake-to-fire interval, and shake orientation. The shaking regimen may be the specific combination of the one or more shake parameters required to be performed on the device in order to deliver, upon actuation of the device, an intended dosage range of a drug. The shaking regimen may be specific for a particular product and may be at least partly dependent on the formulation of the drug, one or more characteristics of the device, the volume of the metering valve, the relative mixing efficiency of the drug particles in the formulation with the excipient(s) and/or propellant(s), or any combination thereof. The shaking regimen may be affected by the composition of the formulation present in the canister (e.g., the number of excipient present with the drug in the formulation or the specific composition of the excipients present in the formulation). Therefore, different products each including the same drug may require very different shaking regimens to deliver an intended dosage range. In some embodiments, the methods provided herein may allow a user or tester of an inhaler or nasal device to identify the specific shake parameters (i.e., shake regimen) required to deliver an intended dosage range of drug from a specific inhaler or nasal device product.

The methods herein may involve monitoring one or more shake parameters of the inhaler or nasal device. The one or more shake parameters may include one or more of shake duration, shake angle, shake frequency, shake-to-fire interval and shake orientation.

The term "shake duration" as used herein may refer to the length of time the inhaler or nasal device is shaken. In some instances, the shake duration may refer to a desired length of time the device should be shaken, e.g. as determined during a shake study using the methods described herein. A desired shake duration may differ for different formulations of drugs (e.g. comprising different active ingredients and/or excipients). In some instances, a desired shake duration may differ for differing devices. A shake duration may be within a range of about 1 second to about 30 seconds. In some instances, a shake duration may be equal to about, or greater than about 1 second, 2 seconds, 3 seconds, 4 seconds, 5 seconds, 6, seconds, 7 seconds, 8 seconds, 9 seconds, 10 seconds, 11 seconds, 12 seconds, 13 seconds, 14 seconds, 15 seconds, 20 seconds, 25 seconds, 30 seconds, 35 second, 40 second, 45 seconds, 50 seconds, 55 second, 60 seconds.

The term "shake angle" as used herein may refer to the angle of the canister of the device during shaking as measured from its vertical axis. For example, a shake angle of 90 degrees would include shaking the canister horizontally. In some instances, the shake angle may refer to a desired angle the device or canister of the device should be shaken in, e.g. as determined during a shake study described in the present disclosure. A desired shake angle may differ for different formulations of drugs (e.g. comprising different active ingredients and/or excipients). In some instances, a desired shake angle may differ for differing devices. A shake angle may be within a range of about 30 degrees to about 180 degrees. In some instances, a shake angle may be equal to, or greater than about 0 degrees, 10 degrees, 20 degrees, 30 degrees, 40 degrees, 50 degrees, 60 degrees, 70 degrees, 80 degrees, 90 degrees, 100 degrees, 110 degrees, 120 degrees, 130 degrees, 140 degrees, 150 degrees, 160 degrees, 170 degrees, 180 degrees.

The term "shake frequency" as used herein may refer to the number of times (cycles) the device is shaken in a given time period. In some instances, the shake frequency may refer to a desired frequency the device should be shaken in a given time period, e.g. as determined during a shake study. A desired shake frequency may differ for different formulations of drugs (e.g. comprising different active ingredients and/or excipients). In some instances, a desired shake frequency may differ for differing devices. A shake frequency may be measured in Hertz (Hz) which is defined as the number of cycles in 1 second. A shake frequency may be within a range from about 1.0 Hz to about 5.0 Hz. In some instances, a shake frequency may be equal to about, or greater than about 0.5 Hz, 1.0 Hz, 1.5 Hz, 2.0 Hz, 2.5 Hz, 3.0 Hz, 3.5 Hz, 4.0 Hz, 4.5 Hz, 5.0 Hz, 6.0 Hz, 7.0 Hz, 8.0 Hz, 9.0 Hz, or 10.0 Hz.

The term "shake-to-fire interval" as used herein may refer to the length of time that occurs between the end of a shaking regimen and the actuation of the device. In some instances, the shake-to-fire interval may refer to a desired length of time that occurs between the end of a shaking regimen and the actuation of the device, e.g. as determined during a shake study. A desired shake-to-fire interval may differ for different formulations of drugs (e.g. comprising different active ingredients and/or excipients). In some instances, a desired shake-to-fire interval may differ for differing devices. A shake-to-fire interval may be within a range from about 0 seconds to about 30 seconds. In some instances, a shake-to-fire interval may be equal to about, or greater than about 0 seconds (i.e., immediate actuation after shaking), 1 second, 2 seconds, 3 seconds, 4 seconds, 5 seconds, 6, seconds, 7 seconds, 8 seconds, 9 seconds, 10 seconds, 11 seconds, 12 seconds, 13 seconds, 14 seconds, 15 seconds, 20 seconds, 25 seconds, 30 seconds, 40 second, 50 seconds, or 60 seconds.

The term "shake orientation" as used herein may refer to an angular range that the device undergoes during shaking. For example, if the device, or canister, is shaken not in an up and down or side to side motion, but in an angular motion, a shake orientation for the device may be relevant. In some instances, the shake orientation may refer to a desired angular range that the device should undergo during shaking. In some instances, the shake orientation may refer to a desired shake orientation of the device, e.g., as determined during a shake study. A desired shake orientation may differ for different formulations of drugs (e.g., comprising different active ingredients and/or excipients). In some instances, a desired shake orientation may differ for differing devices. A shake orientation may be within a range from about 0 to about 359 degrees. In some instances, a shake orientation may be equal to about, or greater than about 0 degrees, 10 degrees, 20 degrees, 30 degrees, 40 degrees, 50 degrees, 60 degrees, 70 degrees, 80 degrees, 90 degrees, 100 degrees, 110 degrees, 120 degrees, 130 degrees, 140 degrees, 150 degrees, 160 degrees, 170 degrees, 180 degrees, 190 degrees, 200 degrees, 210 degrees, 220 degrees, 230 degrees, 240 degrees, 250 degrees, 260 degrees, 270 degrees, 280 degrees, 290 degrees, 300 degrees, 310 degrees, 320 degrees, 330 degrees, 340 degrees, 350 degrees, or 360 degrees.

In some examples, the appropriate shaking regimen for a particular inhaler or nasal device products may be unknown. The methods herein may involve testing a specific inhaler or nasal device product in order to determine the appropriate shaking regimen, for example, by monitoring or measuring one or more shake parameters of the inhaler or nasal device, and then measuring the emitted dose of drug after actuation of the device. Methods of measuring the emitted dose of drug and determining the dose content uniformity performance of the device are described below.

In some embodiments, determining an appropriate shaking regimen may involve adjusting one or more shake parameters and measuring an emitted dose of drug from the device after actuation. In some cases, the effect of a single shake parameter on the performance of a device may be tested (e.g., shake angle). In such cases, the methods may involve shaking the inhaler or nasal device at a defined shake angle (e.g., 30 degrees), actuating the device, and recording the emitted dose, then subsequently shaking the device at a different shake angle (e.g., 40 degrees), actuating the device, and recording the emitted dose. This method may be repeated a plurality of times, each time varying the shake angle and recording the emitted dose. The method may then be used to determine the appropriate shake angle required to emit a target dosage range of drug. The method can be used to test the performance of an inhaler or nasal device with any number of shake parameters as described herein. In some cases, one, two, three, four, or five shake parameters are tested. In some cases, combinations of shake parameters may be tested (e.g., testing a specific combination of shake angle and shake frequency required to emit a target dosage range of drug).

The methods described herein may include actuating the device, after a shaking regimen has been performed, to release an amount of the formulation. In some cases, the formulation is released from the inhaler or nasal device in a spray. The spray may contain an emitted dose of a drug. The term "actuation" may refer to the act of compressing the canister of an inhaler or nasal device for a period of time to release a substance contained within the canister or the holder of the device. Actuation may be, for example, automated actuation or hand actuation.

Actuation of the device, for example, may release a single dose of a formulation contained therein. Proper actuation of the device may be required to release a target dosage of drug from the device. For example, an inhaler or nasal device that has been properly shaken according to a prescribed shaking regimen may deliver an unintended dosage of drug if the device is not properly actuated. As such, the methods provided herein may involve measuring or monitoring actuation of the inhaler or nasal device. Actuating an inhaler or nasal device may include one or more actuation parameters. The one or more actuation parameters may include, without limitation, compression velocity, compression acceleration, actuation hold time, decompression velocity, decompression acceleration, actuation stroke length, and any combination thereof. Thus, measuring or monitoring actuation of an inhaler or nasal device may involve measuring or monitoring one or more actuation parameters.

"Compression velocity" as used herein may refer to the speed with which the device is compressed (e.g., the speed with which a user pushes or compresses the canister or nasal actuator during actuation). Compression velocity may be from about 10 mm/s to about 100 mm/s. For example, compression velocity may be about 10 mm/s, 15 mm/s, 20 mm/s, 25 mm/s, 30 mm/s, 35 mm/s, 40 mm/s, 45 mm/s, 50 mm/s, 55 mm/s, 60 mm/s, 65 mm/s, 70 mm/s, 75 mm/s, 80 mm/s, 85 mm/s, 90 mm/s, 95 mm/s, 100 mm/s or greater than 100 mm/s.

"Compression acceleration" as used herein may refer to the rate of change in velocity per unit time of the canister or nasal actuator during compression. Compression acceleration may be from about 500 $mm/s^2$ to about 4000 $mm/s^2$. For example, compression acceleration may be about 500 $mm/s^2$, 600 $mm/s^2$, 700 $mm/s^2$, 800 $mm/s^2$, 900 $mm/s^2$, 1000 $mm/s^2$, 1100 $mm/s^2$, 1200 $mm/s^2$, 1300 $mm/s^2$, 1400 $mm/s^2$, 1500 $mm/s^2$, 1600 $mm/s^2$, 1700 $mm/s^2$, 1800 $mm/s^2$, 1900 $mm/s^2$, 2000 $mm/s^2$, 2100 $mm/s^2$, 2200 $mm/s^2$, 2300 $mm/s^2$, 2400 $mm/s^2$, 2500 $mm/s^2$, 2600 $mm/s^2$, 2700 $mm/s^2$, 2800 $mm/s^2$, 2900 $mm/s^2$, 3000 $mm/s^2$, 3100 $mm/s^2$, 3200 $mm/s^2$, 3300 $mm/s^2$, 3400 $mm/s^2$, 3500 $mm/s^2$, 3600 $mm/s^2$, 3700 $mm/s^2$, 3800 $mm/s^2$, 3900 $mm/s^2$, 4000 $mm/s^2$ or greater than 4000 $mm/s^2$.

"Actuation hold time" as used herein may refer to the amount of time a device is held in its fully actuated state. "Fully actuated" may refer to maximal compression of the canister of an inhaler or nasal device. Actuation of a device may include compression of a device and may include an "actuation hold time window", for example, a period of time in which a device is held in its fully actuated state. An actuation hold time window may be from about 0 seconds to about 30 seconds. For examples, an actuation hold time window may be about, for example, 0 seconds (immediate release), 1 second, 2 seconds, 3 seconds, 4 seconds, 5 seconds, 6 seconds, 7 seconds, 8 seconds, 9 seconds, 10 seconds, 11 seconds, 12 seconds, 13 seconds, 14 seconds, 15 seconds, 16 seconds, 17 seconds, 18 seconds, 19 seconds, 20 seconds, 21 seconds, 22 seconds, 23 seconds, 24 seconds, 25 seconds, 26 seconds, 27 seconds, 28 seconds, 29 seconds, 30 seconds or greater than 30 seconds.

"Decompression velocity" as used herein may refer to the speed with which the device is decompressed (e.g., speed with which a user releases or decompresses the canister or nasal actuator after actuation). Decompression velocity may be from about 10 mm/s to about 100 mm/s. For example, decompression velocity may be about 10 mm/s, 15 mm/s, 20 mm/s, 25 mm/s, 30 mm/s, 35 mm/s, 40 mm/s, 45 mm/s, 50 mm/s, 55 mm/s, 60 mm/s, 65 mm/s, 70 mm/s, 75 mm/s, 80 mm/s, 85 mm/s, 90 mm/s, 95 mm/s, 100 mm/s or greater than 100 mm/s.

"Decompression acceleration" as used herein may refer to the rate of change of velocity per unit time during decompression of the canister or nasal actuator during decompression. Decompression acceleration may be from about 500 $mm/s^2$ to about 4000 $mm/s^2$. For example, decompression acceleration may be about 500 $mm/s^2$, 600 $mm/s^2$, 700 $mm/s^2$, 800 $mm/s^2$, 900 $mm/s^2$, 1000 $mm/s^2$, 1100 $mm/s^2$, 1200 $mm/s^2$, 1300 $mm/s^2$, 1400 $mm/s^2$, 1500 $mm/s^2$, 1600 $mm/s^2$, 1700 $mm/s^2$, 1800 $mm/s^2$, 1900 $mm/s^2$, 2000 $mm/s^2$, 2100 $mm/s^2$, 2200 $mm/s^2$, 2300 $mm/s^2$, 2400 $mm/s^2$, 2500 $mm/s^2$, 2600 $mm/s^2$, 2700 $mm/s^2$, 2800 $mm/s^2$, 2900 $mm/s^2$, 3000 $mm/s^2$, 3100 $mm/s^2$, 3200 $mm/s^2$, 3300 $mm/s^2$, 3400 $mm/s^2$, 3500 $mm/s^2$, 3600 $mm/s^2$, 3700 $mm/s^2$, 3800 $mm/s^2$, 3900 $mm/s^2$, 4000 $mm/s^2$ or greater than 4000 $mm/s^2$.

"Actuation stroke length" as used herein may refer to the maximum amount the device is compressed during actuation. In some cases, the actuation stroke length is the mechanical compression limit for the device. Actuation stroke length may be from about 3 mm to about 20 mm. For example, actuation stroke length may be about 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm or greater than 20 mm.

In some examples, the appropriate actuation parameters for a particular inhaler or nasal device products may be unknown. The methods herein may involve testing a specific inhaler or nasal device product in order to determine the appropriate actuation parameters, for example, by monitoring or measuring one or more actuation parameters of the inhaler or nasal device, and then measuring the emitted dose of drug. Methods of measuring the emitted dose of drug and determining the dose content uniformity performance of the device are described below. In some embodiments, determining the appropriate actuation parameters may involve adjusting one or more actuation parameters and measuring an emitted dose of drug from the device. In some cases, the effect of a single actuation parameter on the performance of a device may be tested (e.g., actuation hold time). In such cases, the methods may involve actuating the inhaler or nasal device for a defined actuation hold time (e.g., 1 second), and recording the emitted dose, then subsequently actuating the device for a different actuation hold time (e.g., 2 seconds), and recording the emitted dose.

This method may be repeated a plurality of times, each time varying the actuation hold time and recording the emitted dose. The method may then be used to determine the appropriate actuation hold time required to emit a target dosage range of drug. The method can be used to test the performance of an inhaler or nasal device with any number of actuation parameters as described herein. In some cases, one, two, three, four, five, or six actuation parameters are tested. In some cases, combinations of actuation parameters may be tested (e.g., testing a specific combination of actuation hold time and compression velocity required to emit a target dosage range of drug). In other cases, one or more shake parameters may be combined with one or more actuation parameters to test the effect of specific combinations of shake parameters and actuation parameters on the performance of an inhaler or nasal device.

The methods may further include measuring or analyzing a spray pattern of a spray of drug formulation released from the device after actuation. Although specific embodiments of measuring spray pattern are provided herein, it is envisioned that any method of measuring, or analyzing the spray characteristics of a spray released from an inhaler or nasal device may be utilized. Accordingly, it is to be understood that as used throughout, a spray pattern may refer to any characteristics of the spray, e.g. including the spray's divergence angle (e.g. plume geometry) as the spray exist the device, the spray's cross-sectional ellipticity, uniformity and particle/droplet distribution. In some cases, measuring the spray pattern of a spray involves measuring the time evolution of a spray plume (e.g., by taking multiple measurements of a spray plume over a period of time).

The spray pattern measurement may be further utilized as key identifiers for determining the appropriateness of shake parameters, e.g. for specific drug formulations and/or differing devices. In some instances, the spray pattern measurements may be utilized to verifying consistency and desired performance of the devices (e.g. oral inhalers, nasal devices, etc) having undergone the shake parameters. In some instances, the spray pattern measurements may be used to determine a dose content uniformity (DCU) performance of the devices. Optionally, the spray pattern measurements may be correlated with DCU. Further, based on the DCU performance and/or the correlation, desired shake parameters described throughout may be determined.

In some instances, an optical spray pattern may be measured or analyzed. Non-limiting examples of measuring an optical spray pattern of a spray may be as described in U.S. Pat. Nos. 6,665,421 and 6,973,199, the disclosures of which are herein incorporated by reference in their entireties. For example, the methods herein may involve measuring an optical spray pattern of a spray by illuminating a spray plume with an illumination device (e.g., a laser), and then capturing an image of the spray plume with an imaging device (e.g., a camera).

Alternative methods of measuring or analyzing spray patterns as known in the art may be utilized. In some cases, impaction-based methods may be used. In one non-limiting example, the methods may involve firing the spray pump at a solid, thin-layer chromatography (TLC) plate having a coating that fluoresces in response to incident ultraviolet ("UV") radiation. The pattern of the spray deposited on the plate may then be analyzed.

In some aspects, the methods described herein involve performing a shaking regimen on the device, monitoring one or more spray parameters of the shaking regimen, and actuating the device when a predetermined threshold of the one or more spray parameters has been reached or exceeded. For example, if a shaking regimen included a shake duration of 5 seconds, a shake angle of 60 degrees, and a shake frequency of 2.0 Hz, the device would be actuated after all three shake parameters of the shaking regimen had been reached. In some cases, if one or more of the shake parameters is not met before actuation of the device, the delivered dose of the drug may be different, in some cases substantially different, than the intended target dose.

In some aspects, the emitted dose of drug (e.g., after actuation of the device) is within about 15% of a target DCU performance of an inhaler or nasal device after performing the methods described herein. Dose content uniformity may refer to the uniformity of emitted drug per actuation, consistent with the label claim of the drug product. Thus, the methods herein provide for determining the DCU performance of an inhaler. The methods further provide for determining and/or selecting one or more shake parameters and/or one or more actuation parameters that are required to provide a DCU performance of an inhaler or nasal device product within about 15% of a target DCU performance. In some cases, the target DCU performance of an inhaler or nasal device is defined by regulatory or industry guidelines (e.g., by the U.S. Food and Drug Administration). In some cases, the emitted dose of drug is within about 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% or even identical to the target DCU performance of the inhaler.

In some embodiments, the methods include selecting one or more shake parameters and/or one or more actuation parameters for a specific inhaler or nasal device product such that the emitted dose of drug is within about 15% of a target DCU performance. In some aspects, the method is repeated one or more times (i.e., one or more of the shaking, monitoring, and actuating steps). In some cases, each emitted dose of drug is within about 15% of a target DCU performance of the inhaler. In some aspects, the method is performed in through-life testing of an inhaler or nasal device, for example, the device is tested at beginning-of-life (BoL), middle-of-life (MoL) and end-of-life (EoL). BoL administration may refer to actuating the device at the beginning of the labeled number of sprays (after any required priming sprays have been wasted, and usually within about the first 5% of the labeled number of sprays), MoL administration may refer to actuating the device at the middle of the labeled number of sprays (within about 45-55% of the labeled number of sprays), and EoL administration may refer to actuating the device at the end of the labeled number of sprays (within the last 95% of the labeled number of sprays). Generally, the shaking regimen, actuation parameters, or both are selected such that each emitted dose at BoL, MoL and EoL is within about 15% of a target DCU performance. Target DCU performance will be dependent on the target dose. The target dose is dependent on the product being tested.

In some cases, the spray pattern data may be used to determine the DCU performance of the inhaler. In some instances, the spray pattern data may be correlated with the DCU performance of the inhaler. In some examples, the spray pattern data may be performed in addition to, or as an alternative to, traditional DCU measurement techniques. In some embodiments, the method herein involves alternating one or more rounds of spray pattern data analysis with one or more rounds of DUC performance measurement.

In one embodiment, the spray pattern area may be plotted relative to the shake parameters, actuation parameters, or both (for a non-limiting example, see FIG. 1). In some cases, dose content uniformity (DCU) performance of said inhaler or nasal device is determined based on said spray pattern by using a correlation, where such correlation may be derived from a suitably robust methodology involving experiment planning, data collection, data processing and statistical analysis of the data as may be described in the examples below, though other means of correlation could be implemented.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Measuring the Effects of Shaking on Pressurized Metered Dose Inhaler (pMDI) Performance Introduction The drive for an approved generic albuterol-based pMDI has significantly increased in recent years due to the cost barrier, patent expiration of reference products, and recently released draft FDA guidance documents. Product usage instructions for all of the current FDA approved albuterol pMDIs may only include non-de script language for shaking the pMDI such as " . . . shake well before each use . . . " with seldom indication for the patient regarding shaking duration, frequency, orientation, shake-to-fire interval, or what the effects might be if the patient doesn't shake the product before use. From a formulation perspective, shaking is critical for suspension pMDIs because the active drug particles in the formulation tend to rapidly sink or rise to the liquid surface due to differences in density or charge polarity from the propellants. Excipients, such as ethanol and oleic acid, are often added to suspension pMDI formulations to provide a more stable suspension of the active drug into the propellant.

Another factor that was used in selecting the particular albuterol pMDIs in this study is that patients are rarely prescribed just one inhaled medication. And since all of these products contain the same active ingredient, albuterol, a doctor/therapist could likely prescribe any of these products to a patient for the same indication thinking that the products are equivalent, when they may not be due to their different excipients (among other physical differences)— and the effect of these differences may influence the performance of the product from a patient perspective. The implications of this type of patient confusion has been well documented in the respiratory literature.

Lastly, the in-vitro spray test methods required to show bioequivalence of pMDI products from a regulatory perspective, particularly dose content uniformity (DCU) and aerodynamic particle size distribution (APSD) through-life testing, are time intensive, complicated, and error-prone. Hence, a faster, more efficient, and less labor intensive performance indicating metric, such as optical spray pattern, would help relieve the testing/characterization burden for pMDI product development and help support the generation of more valuable DCU and APSD measurements.

Methods

Three different reference products containing albuterol sulfate were tested through life following a 3 variable, 3 level Box-Behnken Design of Experiments ("BB-DoE") approach. Table 1 below shows the derived control ranges employed to determine the effects of shaking (duration, angle, and frequency) on spray pattern in BB-DoE coded formats. Three canisters per product were tested using 13 variable shaking combinations that were inputted into Viota® software methods and executed using a SprayVIEW® measurement system SFpMDI (Proveris Scientific, Marlborough, MA U.S.A.).

TABLE 1

BB-DoE control variable ranges for tested shake parameters.

| Control Variable | BB-DoE Value | | |
|---|---|---|---|
| | − | 0 | + |
| Shake Frequency (Hz) | 2.0 | 3.0 | 4.0 |
| Shake Angle (deg) | 60 | 90 | 120 |
| Shake Duration (s) | 5 | 10 | 15 |

Using the same shaking regime for each product, an experiment alternating actuations for spray pattern and DCU collection was designed to see if optical spray pattern and DCU are statistically correlated. This study involved collecting ten actuations each at the beginning, middle, and end of life on three (3) cans for each product. Additionally, a DCU through-life experiment was conducted for the product with no excipients using a "shake vs. no shake" comparison where the "shake" parameters were derived from the optical spray pattern DoE results. In these studies, each DCU sample was collected following the protocol outlined in the United States Pharmacopeia using an alternative dose uniformity sampling apparatus and quantified using a spectrophotometric method (ThermoFisher GENESYS 10S UV-Vis Spectrophotometer). Alternatively, other appropriate measurement methodologies may be used (e.g., high performance liquid chromatography).

Results

The consolidated results from the multi-dimensional spray pattern DoE are shown in FIG. 1. Briefly, FIG. 1 depicts a "sensitivity plot" of the spray pattern area plotted against the shaking parameters for each pMDI product (indicated by the number of excipients where Product A had no excipients, Product B had 1 excipient, and Product C had 2 excipients). Table 2 below summarizes the sensitivity analysis in simple "yes" or "no" terms based on statistical p-value analysis.

TABLE 2

Simplified optical spray pattern area sensitivity results.

| Number of excipients | Shake Angle | Shake Frequency | Shake Duration |
|---|---|---|---|
| 0 | No | No | Yes |
| 1 | Yes | No | No |
| 2 | No | No | No |

The results clearly indicate that the products produce vastly different sized spray patterns under identical test conditions with Product A producing the smallest patterns (mean value of about 132 $mm^2$) and Product C producing the largest (mean value of about 350 $mm^2$). The results also indicate that Product A has acute sensitivity to shake duration (about a 20% change in spray pattern area when the device was shaken before each actuation for 5 seconds compared to 15 seconds), while Product B has some sensitivity to shake angle. This result is significant since shake duration is not indicated in any of the product's respective patient usage instructions. Product C seems immune to shaking within the tested range. However, this product did exhibit substantially more shot-shot variation than the others and this variation may be masking the product's true sensitivity.

Results from DCU through-life testing of Product A (no excipients) are shown in FIG. 2 and FIG. 3 where "no shake" indicates that the product samples were not shaken at any point during the experiments; and "shake" indicates that the product samples were shaken with set parameters (10 second duration, 60 degree angle, and 4 Hz frequency) prior to automated actuation. In all cases the product samples were allowed to rest for 3 minutes (180 seconds) between consecutive automated actuations.

The results show a startling effect of not shaking the product on DCU performance: the emitted dose during beginning of life is considerably variable and nearly three times the target value (108 mcg) before it starts to taper off at the middle and end of life stages. However, since so much excess drug was emitted during BoL, the EoL performance shows only about 25% of the target dose is being delivered as shown in FIG. 3. In contrast, the "shake" data indicates very consistent and very near target DCU performance from the product at all life stages.

CONCLUSIONS

The DCU and optical spray pattern performance of three different commercially available albuterol pMDI products were shown to have markedly different sensitivities to shaking. The product with no added excipients produced the smallest optical spray patterns and was sensitive to shake duration—a parameter not included in any of the product's patient usage instructions. Additionally, the effects of not shaking the product without excipients were profound—nearly 3 times the target DCU was measured at the beginning of life which resulted in only about 25% of the target dose being delivered at the end of life. Current patient instructions for the respective products do not include specified guidelines on shaking (particularly shake duration) or the effects of not shaking the product, which were shown here to be rather profound with respect to DCU on one product. However, by providing more defined instructions on how to shake and the importance of shaking, patient confusion could be reduced and more effective patient usage could occur.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of determining usage instructions for an inhaler or nasal device comprising a drug formulation, said method comprising:

a) monitoring or measuring one or more shake parameters of shaking said inhaler or nasal device;

b) actuating said inhaler or nasal device, thereby emitting a spray of said drug formulation, when said one or more shake parameters have been met;

c) measuring a spray pattern of said spray of said drug formulation, wherein said spray of said drug formulation comprises an emitted dose of a drug;

d) determining dose content uniformity (DCU) performance of said inhaler or nasal device by using a correlation with said spray pattern; and e) determining said usage instructions when said DCU performance of said inhaler or nasal device is within 15% of a target dose content over the life of said inhaler or nasal device, wherein said usage instructions comprise said one or more shake parameters.

2. The method of claim 1, further comprising adjusting said one or more shake parameters until said DCU performance of said inhaler or nasal device is within 15% of said target dose content over the life of said inhaler or nasal device.

3. The method of claim 1, wherein said one or more shake parameters are selected from the group consisting of: shake duration, shake angle, shake frequency, shake-to-fire interval, shake orientation, and any combination thereof.

4. The method of claim 1, wherein said actuating comprises one or more actuation parameters.

5. The method of claim 4, further comprising measuring or monitoring said one or more actuation parameters.

6. The method of claim 5, further comprising adjusting the one or more actuation parameters until said DCU performance of said inhaler or nasal device is within 15% of said target dose content over the life of said inhaler or nasal device.

7. The method of claim 4, wherein said usage instructions comprise said one or more actuation parameters.

8. The method of claim 4, wherein said one or more actuation parameters are selected from the group consisting of: compression velocity, actuation hold time, decompression velocity, decompression acceleration, actuation stroke length, and any combination thereof.

9. The method of claim 1, wherein said determining of e) comprises determining said usage instructions when said DCU performance of said inhaler or nasal device is within 10% of a target dose content over the life of said inhaler or nasal device.

10. The method of claim 1, wherein said determining of e) comprises determining said usage instructions when said DCU performance of said inhaler or nasal device is within 5% of a target dose content over the life of said inhaler or nasal device.

11. The method of claim 1, further comprising providing said usage instructions to a subject.

12. The method of claim 1, comprising performing a)-d) on said inhaler or nasal device at beginning of life, at middle of life, and at end of life of said inhaler or nasal device.

13. The method of claim 12, wherein said determining of e) comprises determining said usage instructions of said inhaler or nasal device when said DCU performance of said inhaler or nasal device is within 15% of a target dose content at beginning of life, at middle of life, and at end of life of said inhaler or nasal device.

14. The method of claim 1, wherein said inhaler or nasal device is selected from the group consisting of: a pressurized metered dose inhaler (pMDI), a metered dose inhaler (MDI), and a nasal spray.

15. The method of claim 1, further comprising determining said usage instructions for a plurality of inhaler or nasal devices, wherein said usage instructions are different for each inhaler or nasal device of said plurality of inhaler or nasal devices.

16. The method of claim 15, wherein each inhaler or nasal device of said plurality of inhaler or nasal devices comprises the same drug.

17. The method of claim 15, wherein each inhaler or nasal device of said plurality of inhaler or nasal devices comprises a different drug formulation.

18. The method of claim 1, wherein said spray pattern comprises a physical or optical characteristic of said spray, a particle or droplet distribution of said spray, or a cross-sectional uniformity of said spray.

19. The method of claim 1, wherein said measuring of c) comprises illuminating said spray with an illumination device and imaging said spray pattern with an imaging device, or measuring a time evolution of a spray plume of said spray.

20. The method of claim 1, wherein said spray pattern is an impaction-based spray pattern or an optical spray pattern.

* * * * *